US006414302B1

(12) United States Patent
Freeouf

(10) Patent No.: US 6,414,302 B1
(45) Date of Patent: Jul. 2, 2002

(54) HIGH PHOTON ENERGY RANGE REFLECTED LIGHT CHARACTERIZATION OF SOLIDS

(75) Inventor: John Lawrence Freeouf, Lewisboro, NY (US)

(73) Assignee: Interface Studies Inc, Katonah, NY (US)

( * ) Notice: Subject to any disclaimer, the term of this patent is extended or adjusted under 35 U.S.C. 154(b) by 0 days.

(21) Appl. No.: 09/160,017

(22) Filed: Sep. 24, 1998

Related U.S. Application Data
(60) Provisional application No. 60/096,017, filed on Aug. 11, 1998.

(51) Int. Cl.$^7$ ............................... G02F 1/01; G01J 4/00
(52) U.S. Cl. ........................................ 250/225; 356/369
(58) Field of Search ................................ 356/364, 369, 356/381; 250/225

(56) References Cited

U.S. PATENT DOCUMENTS

| | | | |
|---|---|---|---|
| 3,880,524 A | 4/1975 | Dill et al. | 356/118 |
| 4,053,232 A | 10/1977 | Dill et al. | 356/118 |
| 4,332,833 A | 6/1982 | Aspnes et al. | 427/8 |
| 4,653,924 A | 3/1987 | Itonaga et al. | 356/369 |
| 4,672,196 A | 6/1987 | Canino | 250/225 |
| 4,762,414 A | 8/1988 | Grego | 356/349 |
| 4,837,603 A | 6/1989 | Hayashi | 365/369 |
| 5,091,320 A * | 2/1992 | Aspnes et al. | 356/369 |
| 5,277,747 A | 1/1994 | Aspnes | 156/626 |
| 5,526,117 A | 6/1996 | Wielisch et al. | 356/369 |
| 5,552,327 A * | 9/1996 | Bachmann et al. | 437/8 |
| 5,582,646 A * | 12/1996 | Woollam et al. | 437/7 |
| 5,595,916 A | 1/1997 | Fujimura et al. | 437/8 |
| 5,608,526 A | 3/1997 | Piwonka-Corle et al. | 356/369 |
| 6,034,777 A * | 3/2000 | Johs et al. | 356/369 |

FOREIGN PATENT DOCUMENTS

| | | | |
|---|---|---|---|
| JP | 63-12906 | * | 1/1988 |
| JP | 64-23105 | * | 1/1989 |
| JP | 5-263244 | * | 10/1993 |

OTHER PUBLICATIONS

R.L. Johnson et al, "Spectroscopic Ellipsometry with Synchrotron Radiation", Review of Scientific Inst. vol. 60 (7) Jul. 1989 pp. 2209–2212.

Germer et al, "Plarization of Out–of–Plane Scattering from Microrough Silicon", Optics Letters, vol. 22 (17) Sep. 1997 pp. 1284–1286.

P.S. Hauge, "Recent Developments in Instrumentation in Ellipsometry," Surface Science, vol. 96, No. 1–3, 1980, pp. 108–140.

Kenneth K. Ellis, "Polarimetric Bidirectional Reflectance Distribution Function of Glossy Coatings," J. Opt. Soc. Am., vol. 13, No. 8, Aug. 1996 pp. 1758–1762.

Deumié et al, "Ellipsometry of Light Scattering from Multilayer Coatings," Applied Optics, vol. 35 No. 28, Oct. 1996, pp. 5600–5608.

(List continued on next page.)

Primary Examiner—Frank G. Font
Assistant Examiner—Zandra V. Smith

(57) ABSTRACT

Accuracy and sensitivity in the optical characterization of solids and solid materials are improved through the use of the interdependent features of: extending the photon energy range over which the metrology is performed to include a portion of the range up through 10 eV, in which, the higher photon energy of the light improves signal distinguishing ability; and providing a controlled ambient in the entire light path between the light source and a detector that prevents absorption and signal definiteness masking so as to sharpen the identifiability of the change parameters imparted into the reflected light. Combinations of specific devices and materials that for different types of ellipsometry are provided.

6 Claims, 3 Drawing Sheets

OTHER PUBLICATIONS

U. Rossow et al, "Interpretation of Surface–Induced Optical Anisotropy of Clean, Hydrogenated, and Oxiioized Vicinal Silicon Surfaces Investigated by Reflectance Difference Spectroscopy," J. Vac. Sci. Tech. B, 14, 4, Jul./Aug./1996 pp. 3070–3074.

John L. Freeouf, "Application of Spectroscopic Ellipsometry to Complex Samples", App. Phys. Ltrs, 53,(24), Dec. 1988 pp. 2426–2428.

D.E. Aspnes, Analysis of Semiconductor Materials and Structures by Spectro Ellipsometry, S.P.I.E. vol. 946, 1988 pp. 84–97.

Sales Brochure, J.A. Woollam Co., Variable Angle Spectroscopic Ellipsometers, 8 pages.

Sales Brochure, "Infrared Spectroscopic Ellipsometer SE 900", SENTECH, Instruments, 4 pages.

T.E. Faber and N.V. Smith, "Optical Measurements on Liquid Metals Using a New Ellipsometer", Journal of the Optical Society of America, vol. 58, No. 1, Jan. 1968, pp. 102–108.

S. Bertucci et al, "Systematic Errors in Fixed Polarizer, Rotating Polarizer, Sample, Fixed Analyzer Spectroscopic Ellipsometer," Thin Solid Films, 313–314 (1998) 73–78.

Azzam et al, "Analysis of Systematic Errors in Rotating–Analyzer Ellipsometers," Journal of the Optical Society of America, vol. 64, No. 11, Nov. 1974, pp. 1459–1469.

* cited by examiner

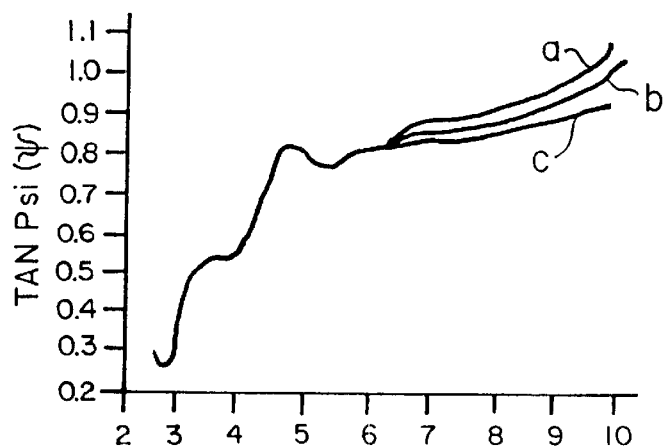
FIG. 2
FIG. 3
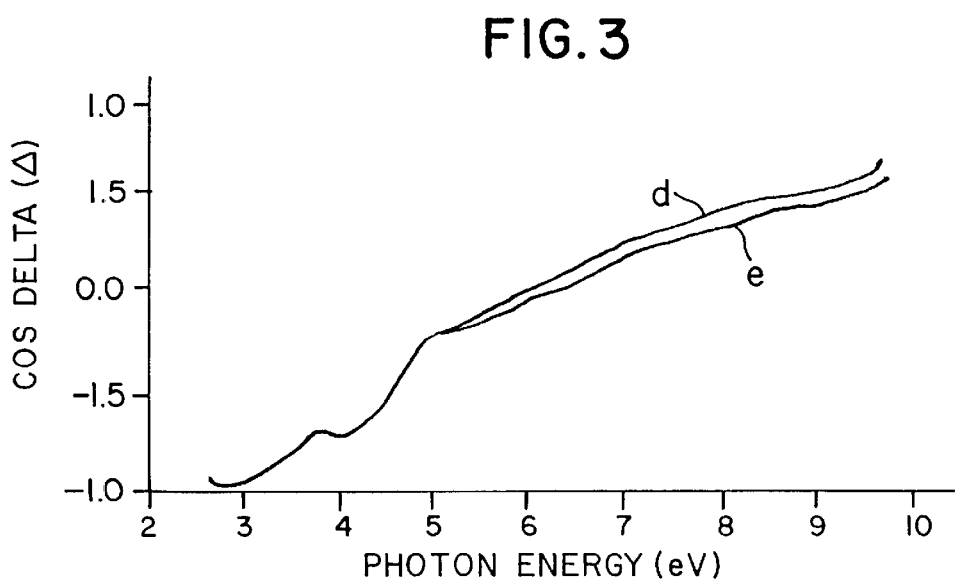
FIG. 4
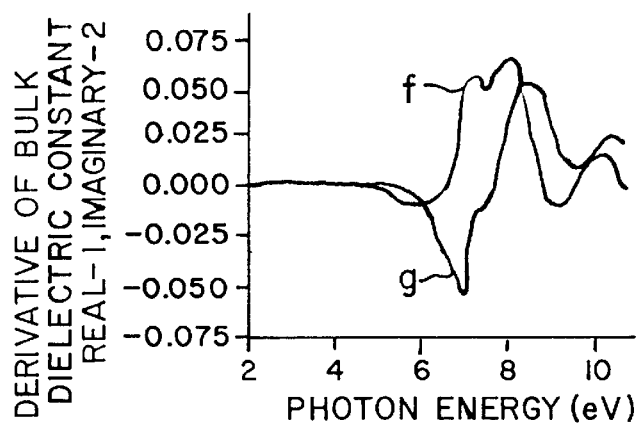

HIGH PHOTON ENERGY RANGE REFLECTED LIGHT CHARACTERIZATION OF SOLIDS

Cross reference is made to applications Ser. Nos. 09/318,035 Filed May 25, 1999; and 09/461,658 Filed Dec. 14, 1999 of the assignee of this invention directed to related subject matter.

This application claims benefit of provisional application Ser. No. 60/096,017 filed Aug. 11, 1998.

FIELD OF THE INVENTION

The invention relates to metrology which in turn involves the technology of the use of reflected light in the investigation of the bulk and surfaces of solids and solid materials; and in particular to the extension of the sensitivity and detectability achievable in that technology.

BACKGROUND OF THE INVENTION AND RELATION TO THE PRIOR ART

Metrology involving the use of reflected light in the identification or characterization of the surface and bulk aspects of solid materials has been receiving considerable attention over a long period in the art. In essence, at the present state of the art, there are two general types of characterization technologies. In a first type, the light is incident to and reflected from the sample under study at a direction that is approximately the vertical or the normal with respect to the surface of the sample. The polarization induced differences in the reflected light that are produced by the sample are the measured quantity. This type of characterization has acquired the name in the art of Reflection Difference Anisotropy and is sometimes identified by the acronym RDA. In a second type, the light is incident to and reflected from the sample under study at relatively large angles with respect to the sample, as compared with the first type. Changes in polarization of a reference polarized light resulting from variations of the angles, and changes in light both in and out of the plane of the device are the measured quantities. This second type includes most ellipsometry techniques.

In a less constrained form of ellipsometry, called herein BiDirectional Ellipsometry, the incident and reflected angles need not be equal. One determines the amplitude and polarization of the reflected beam as a function of the polarization, wavelength and angle of incidence of the incident beam, as well as of the deviation of the measured direction from the specular (defined as equal to the angle of incidence) beam. This deviation being defined in the two directions of "within" and "perpendicular to", the plane of incidence. While the principles are useful in many types of characterization measurements, each situation in which the principles are applied will involve a number of considerations that are unique to that situation. In order to establish a perspective in the application of the technology; the semiconductor industry is used as an illustration for the reasons that the technology is quite amenable to such considerations as the dimensions being small, that the characterization of the material under study usually be nondestructive and that there be an ability to make monitoring determinations in real time.

In the semiconductor industry the principles of ellipsometry have been extensively applied to the types of material characterizations needed to meet the ever decreasing dimensions encountered in devices and in their fabrication.

In the 1980 timeframe, P. S. Hauge in an article titled "Recent Developments in Instrumentation in Ellipsometry" in Surface Science, Vol. 96 (1980), pages 108–140 provided a survey of the instrumentation available in the art at that time.

In the 1988 timeframe, D. E. Aspnes, in an article titled "Analysis of Semiconductor Materials and Structures by Spectroellipsometry" in SPIE Vol. 946III pages 85–97; provided an anthology of the state of the art at that time for various types of material characterizations and data analytical techniques.

Also in 1988, R. L. Johnson et al, in an article titled "Spectroscopic Ellipsometry with Synchrotron Radiation" in Review of Scientific Instruments 60, 7, July 1988 Pages 2209–2212 described the use of high photon energy syncrotron radiation in ellipsometry on InP, Y $Ba_2Cu_3O_7$ and $CaE_2$. By the approximately 1994 timeframe, U.S. Pat. No. 5,526,117 indicated that the art had progressed to dimensions in the vicinity of the 100 nanometer (nm) range.

In 1997, Germer et al. in an article titled "Polarization of out-of-plane scattering of microrough silicon", in Optics Letters, Vol. 22 No. 17, Sept. 1997, pages 1284–1286, indicates the advantages of polarization information that is out of the plane of the device, i.e., BiDirectional. ellipsometry.

There are metrology companies such as Sentech in Germany, and Woollam in the U.S., that have strong programs and ellipsometric metrology products in the marketplace.

The present technology has been yielding satisfactory results where the dimensions under study are above tens of nanometers (nm) but it is becoming increasingly difficult to get the accuracy needed. Current expectations are toward gate widths of the order of 0.25 micrometers in 1998, progressively becoming narrower to about 0.1 micrometers by 2007. Dielectric thicknesses must shrink to meet the line widths for a gain in performance to be realized. The dielectric thickness must therefore shrink from about 4.0 nm in 1998 to about 1.5 nm in 2007. Further such dimensions will probably be made up of several thinner layers. Metrology is a necessary corrolary to achieving these technologies. It is necessary to be able to measure a dimension in order to be able to properly control it. The thicknesses and tolerances predicted cannot be properly characterized with current technologies. The limitations of the equipment presently in use in the art has resulted in photon energy ranges of less than 6 eV, beyond which the light is not transmitted to the detector and the ability to distinguish is limited. Such a situation is present in the semiconductor industry wit the types of dielectrics being used. Progress at this point in time however is primarily being directed to using extended range reflectometry applied to current techniques, and the goals are primarily to characterize optical properties at lithography wavelengths such as 193 nm.

SUMMARY OF THE INVENTION

Improvements is accuracy and sensitivity in the optical characterization of solids and solid materials are achieved through the use of the interdependent features of: extending the photon energy range over which the metrology is performed to include; the range up through about 10 eV, in which, the higher photon energy of the light improves signal distinguishing ability; providing a controlled ambient in the entire light path between the light source and a detector that prevents absorption and signal definiteness masking so as to sharpen the identifiability of the change parameters imparted into the reflected light. There are provided combinations of specific devices and materials that define the features in the characterization.

BRIEF DESCRIPTION OF THE DRAWINGS

FIGS. 2 to 4 are graphs of signals of highly useful analytical surface and bulk solid material characterization parameters, illustrating advantages in the extended photon energy range in the invention; wherein:

FIG. 2 is a graph of Photon energy (eV) vs Tan Psi ($\Psi$) illustrating the divergence of the signal that occurs in the range beyond about 6 eV photon energy.

FIG. 3 is a graph of Photon energy (eV) vs Cos Delta ($\Delta$) illustrating a divergence of the signal that occurs in the range beyond about 5 eV photon energy.

FIG. 4 is a graph of Photon energy (eV) vs the derivatives of real and imaginary bulk dielectric constants indicating that different paths are followed in the range above 6 eV photon energy.

DESCRIPTION OF THE INVENTION

In the reflected light characterization of the invention; the photon energy range of the light is extended to include energies where optical and physical properties of the material in the sample under study produce unique signal changes and a controlled ambient is provided that prevents absorption and masking of the definitiveness of those signal changes. The signal changes in turn permit identification and quantification of surface, bulk and reflection properties of the material involved. In accordance with the invention it has been found that curves of significant signal variations related to the properties of materials, when the range of photon energy of the light to be reflected is extended into the range through and including 10 eV, diverge, and thereby make possible, in the controlled ambient, the detection and evaluation of material properties to an extent that has not been available heretofore in the art.

Figure 1:
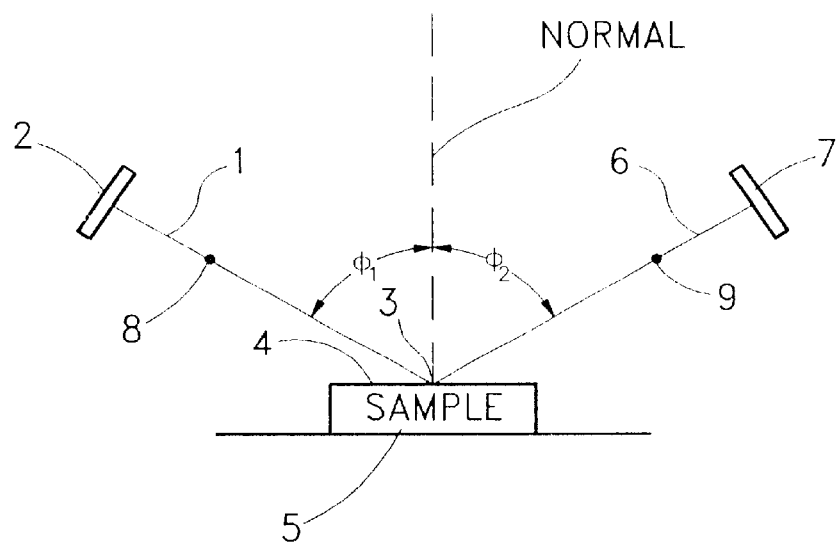
FIG. 1, labelled prior art, is a schematic illustration of the features involved in typical characterization of solids and solid materials.

Referring to FIG. 1 there is shown a schematic illustration of the features involved in the typical types of reflected light characterization of solids and solid materials, as reflected light characterization has been practiced heretofore in the art. Incident light from a light source is reflected from the surface of a sample of a material under study and changes are detected that indicate differences in the properties of the sample. In FIG. 1 incident light 1, from a relatively low, less than about 6 eV photon energy source 2, and reflected at 3 from the surface 4 of a sample 5 of a solid material under study. The reflected light 6 from the sample 5 is sensed in a detector 7. The incident light beam is initially ploarized at 8 and changes in polarization are analyzed at 9. The detector 7 receives the output signal of the analysis at 9.

There are a wide range of components such as light sources, light windows, light filters, polarization devices, detectors and photomultipliers that are employed in the present metrology in the art. In the metrology of FIG. 1 the typical light source 2 is a Xenon arc lamp which loses usefulness at about 7 eV; typical windows are Quartz which has a cut-off at about 6–7 eV, and the typical polarizer is Calcite which has a cut-off about 5.5 eV. Atmospheric absorption restricts the operation to energies less than about 6.5 eV.

In reflected light characterization, the light, which is a band, is reduced to a single defined frequency with a monochronometer, not shown, or through the use of a laser as a source, such as is standard in the art. Where a monochrometer is used it can be placed after the light source in the incident light path or before the detector in the reflected light path.

In the Reflection Difference Anisotropy (RDA) type of characterization analysis the angle $\Phi_1$ of the incident light 1 and the angle $\Phi_2$ of the reflected light 6 are equal with respect to relationship to the perpendicular or the normal with the surface 4 of the sample 5. In this type of characterization analysis, the separation from the vertical of both the incident and reflected light is small, much smaller than the scale of FIG. 1 would indicate, the combination subtending only about 5 degrees. The polarization dependent parameter that is measured is a small variation both in the amplitude and phase of the reflected light produced by the variations in the sample that are under study. This is typically studies as a function of wavelength of the light.

In the ellipsometric types of characterization analysis, of which there are several, there are a wider range of parameters involved. The angles of the light, the plane of the measurements, the state of polarization and the light wavelength are monitored. The parameters measured are the intensity and the state of polarization in the reflected light compared to the incident light In the BiDirectional Ellipsometry type of ellipsometric characterization analysis, frequently referred to in the art by the acronym BDE, as one example, the angles $\Phi_1$ and $\Phi_2$, are not equal and some signals vary over a substantial range, with variations in a ratio of the distance of a feature location in the material under study to the wavelength of the light being monitored. In the Reflection Difference Anisotropy (RDA) types of characterization analysis, the measurement is difference in reflection, however the light could be provided with polarization at either or both of locations 8 or 9 that would improve the identifiability at the detector 7 of the difference in reflection of the reflected light 6.

In the ellipsometrical types of characterization analysis, the measurement includes difference in polarization so that the incident light 1 would be provided with a reference polarization at location 8 and changes from that reference polarization would be identified in the reflected light path at location 9.

Heretofore in the art the range of influencing factors has resulted in a very large quantity of data to be processed in any analysis. The data then is reduced by an iterative progressive fitting algorithm in which assumed values are incrementally adjusted to reduce differences from measured values. Under these circumstances it will be apparent that the ability to distinguish particular properties of the sample under study will be limited by many factors including the approach to the limits of usefulness of the components, and any extraneous noise, produced for example by light scattering.

Figure 5:
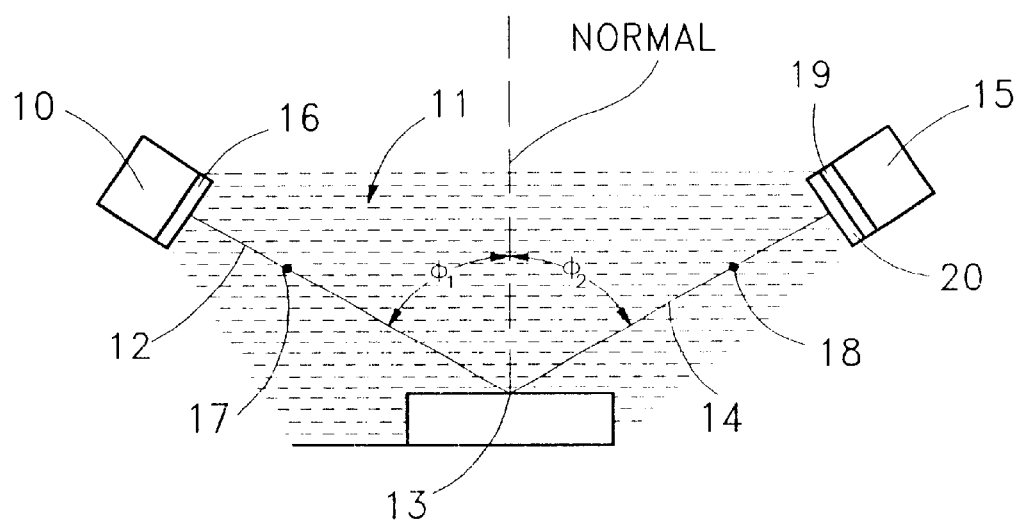
FIG. 5 is a schematic illustration of the principles involved in the surface and bulk solid material characterization of the invention.
Figure 6:
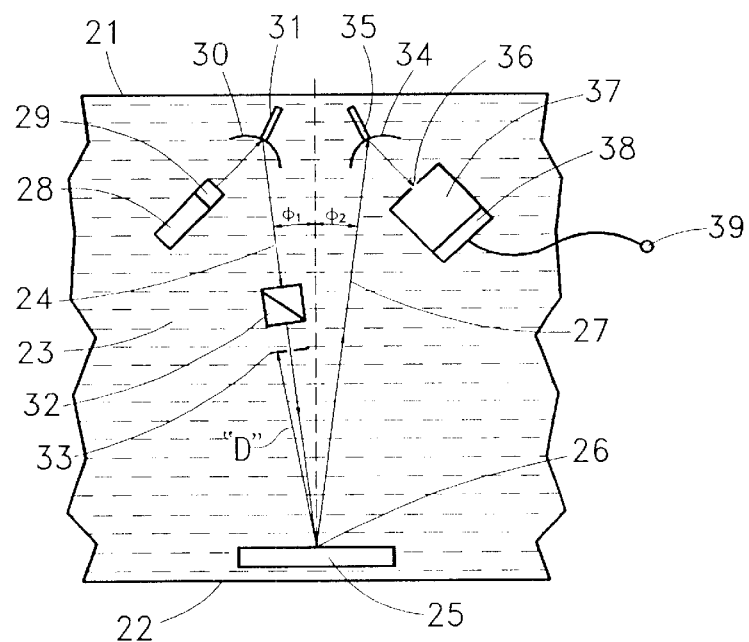
FIG. 6 is a schematic illustration of a detailed Reflection Difference Anisotropy (RDA) embodiment of the invention.
Figure 7:
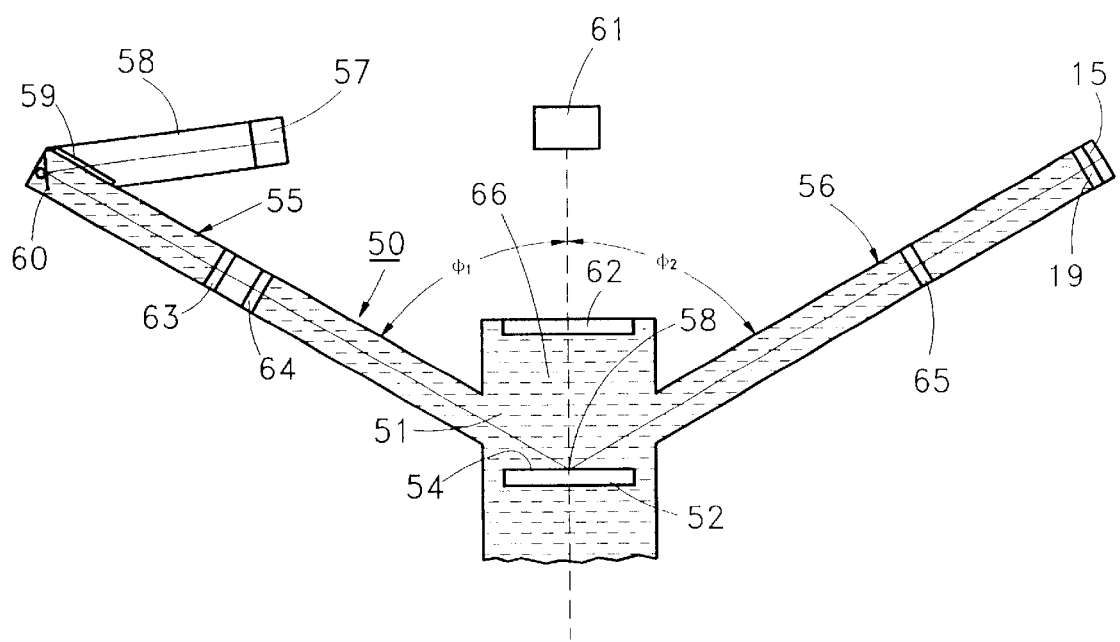
FIG. 7 is a schematic illustration of a detailed ellipsometric embodiment of the invention.

While the illustrations of FIG. 1 and the to be described FIGS. 5, 6 and 7 are portrayed in the standard two dimensional diagrams used in the art it will be apparent to one skilled in the art, that in the light of the advantages of the "out-of-plane" metrology as set forth by the Germer et al. reference described above, three dimensional directions may become involved. While such "out-of-plane" metrology adds complexity to the mathematics of the analysis the added complexity is far outweighed by advantages in sensitivity and distinguishability.

In accordance with the invention, the photon range of the light being reflected, is extended by providing a higher photon range source of light, together with providing an entire light path from the point source in the light, through the reflection, to the detector, with a controlled ambient that minimizes the effect of any absorption and any masking of the ability to detect and quantify any differences sensed in the reflected light from that in the incident light path. In reflected light characterization of solid materials, when practiced in that higher photon range and in the controlled ambient of the invention, there is a sharp improvement in sensitivity, in signal distinguishing ability and in analysis. In FIGS. 2, 3 and 4 graphs of unique characterization signal performance occurring at a range of light photon energy that is up through and including 10 eV in the controlled ambient of the invention are provided. The unique signal performance is correlatable with the types of information essential in the characterization, or identification of quality features of the composition, of the surface and of the bulk of a sample of a material under study. The graph scales and the discussion are directed as perspective examples of the analysis of a small dimension sample of a material, of the order of 5 nanometers or less, such as would be encountered in the characterization of the gate insulator of a semiconductor field effect transistor. Referring to FIG. 2 a graph is provided in which there is provided as a function of the photon energy (eV), the standard ellipsometry signal Tan Psi ($\Psi$), which is the ratio of the two polarization dependent reflection coefficients and one of the variables measured by ellipsometry, showing the type of correlation available with the extended photon range ellipsometry of the invention in which illustrative properties of particular layers in a sample of a material are distinguished.

In FIG. 2 there is a single signal in the eV range below above 6 eV, which is about the upper limit of conventional ellipsometry. In that signal, the differences are too small to be seen on the graph, whereas, within the range above 6 eV the signal diverges into three separate traces a, b and c, each of which is identifiable with a property of a material of a sample. As an illustration. consider the data to be describing a three layer oxide/nitride/oxide structure on a substrate with a total thickness of about 4.0 nm such as used in the art to prevent dopant depletion, reduce interface roughness and improve pinhole hardness, with the thickness divided between the three layers. Although five separate structures are involved only three types of curves are seen because the controlling variable is the total thickness. There is a first layer of silicon dioxide ($SiO_2$) on the substrate, there is a center layer of silicon nitride ($Si_3 N_4$) and there is a surface layer of silicon dioxide ($SiO_2$). The total dielectric thickness is fixed at 4.0 nanometers in each of the samples so that the layer thickness variations are only in the individual layers of $SiO_2$ and the $Si_3 N_4$ center layer.

In the single curve, below about 6 eV, differences between the structures, a, b and c, were not distinguishable but in the range above 6 eV, there is divergence into three, separate, readily distinguishable curves labelled a, b, and c, corresponding to the specific samples. Sample a is a structure of a 2.0 nm layer of $SiO_2$ on a 0.5 nm layer of $Si_3 N_4$ that in turn is on a 1.5 nm layer of $SiO_2$. Sample b is a structure of a 2.0 nm layer of $SiO_2$ on a 1.0 nm layer of $Si_3N_4$ that in turn is on a 1.0 nm layer of SiO. Sample c is a structure of a 2.0 nm layer of SiO on a 1.5 nm layer of Si N that in turn is on a 0.5 nm layer of SiO. The divergences of the branches a, b. and c at 10 eV photon energy light is such that a difference in thickness range of the SiO layer next to the substrate varied from 0.5 to 1.5 nm; while the top layer remained constant at 2.0 nm; produced a readily identifiable, almost 0.3 difference in value of Tan Psi ($\Psi$).

Referring to FIG. 3 a graph is shown illustrating the increased analysis sensitivity achieved with the extended photon range ellipsometry of the invention. In FIG. 3 the graph is of Photon energy (eV) vs the standard ellipsometry output signal Cosine Delta ($\Delta$), and illustrates the use of the invention in the metrology of changing the thickness of the nitride layer in a 4 nm sample of oxide/nitride/oxide on a substrate while maintaining constant thickness. The graph indicates a single curve in in the range up to about 5 eV with some sensitivity and thereafter a greater sensitivity and a divergence into separate branches, d and e, in the extended photon range. The divergence of the signal into the d and e branches is sensitive to the thickness dimension of an individual layer of the sample of material.

Considering the sample of material in FIG. 3 to be of three layers on a silicon substrate. If there is a 2.0 nm surface layer of SiO on a 1.5 nm layer of Si N that in turn is on a 1.0 nm layer of SiO on a substrate such as Si; then the curve of branch d would be produced. When the thickness of the center, Si N layer is reduced from 1.5 nm to 1.0 nm the curve follows the branch e. The difference between the branches d and e at the higher photon energy range result in a difference of about 0.02 in the Cosine Delta ($\Delta$) value for use in characterization analysis. The gains follow in part from reduced wavelength of the higher energy photons and they are also due in part to the fact that optical prpoerties of constituents all change substantially in the higher photon energy range. For example $SiO_2$ and $Si_3 N_4$ both become highly absorbing whereas the dielectric functions of Si are smaller in the higher photon ranges of the lower photon range of up to 6 eV used heretofore in the art. This provides a larger range of variation of parameter space with which to perform analysis.

Referring to FIG. 4 a graph is provided of the values of the real and the imaginary derivatives of the bulk dielectric constant of an example material (SiC) vs the photon energy (eV) illustrating the fact that in the extended photon range of the invention the curves representing the values of the real, f, and of the imaginary, g, derivatives take independent and completely distinguishable paths. The branches f and g begin to diverge about 4 eV and take completely different paths in the higher eV ranges. For many material surfaces the derivative of the bulk dielectric constant is a measure of the surface condition and the magnitude of the signal represented by the curve can be scaled to a measure of step density. The divergent paths of FIG. 4 permit, in an analysis, the distinction of surface and interface roughness, island formation and steps, and are of particular value where the material under study has a high band gap such as silicon carbide (SiC) and Gallium Nitride (GaN). Signals of the type in FIG. 4 may be used in predictions of the applications of the techniques of the invention to SiC.

The characterization capability of the invention involves the interdependent providing of a somewhat limited range of higher photon energy light together with attenuation and absorption control of any source of output signal masking throughout the entire light path. In accordance with the invention, the sources that may affect output signal definiteness masking, include unwanted excitation aspects of the production of the higher photon energy light from being included in the incident light beam, and, any ingredient in the ambient interacting with the light source; any absorption and any excitation in the ambient through the entire light path, any unwanted aspects of the detection of the output signal entering the ambient and any property changes of the materials used in components such as beam splitters, windows and filters, from passage of the high energy light.

The range of higher energy light used with the invention is in the range of up through and including 10 eV. In that range the signal benefits are achieved while detrimental aspects such as destruction of the type of dilectrics used in the semiconductor industry is controllable with normal ambient control conditions such as an inert gas or normal vacuum. As an illustrative contrast there is reported, in the 1988 Johnson et al reference discussed in the background above, metrology in which there is the use of very high photon energy light, in the 30 eV range produced through the very expensive synchrotron radiation. In accordance with this invention as the light energy increases control of the ambient becomes more demanding in order to retain distinguishability of the signal. At the 30 eV level the Johnson et al article reported the need for a difficult to maintain high vacuum ambient. The synchrotron must operate at the ultra high vacuum, and it's expense requires the high vacuum to be protected against accidental exposure to atmosphere in experimental or production operations with it. One mode of such protection is to couple the synchrotron to the experimental or production apparatus through a solid window that transmits the necessary photons. At the present state of the art there appears to be no solid that transmits a continuum to higher photon energies than the LiF window which cuts off at about 10 eV so that this would be the likely high energy limit of a synchrotron system not fully under vacuum.

It will be apparent that the terminology in the invention specifying a controlled ambient is relative and involves pragmatism in the following way. The effect of the ambient on the characterization ability involves both the length of the optical path as well as with any interaction affecting the information in the light along the way and the required sensitivity to get the desired information.

In accordance with the invention the entire optical path from the light source to the detector is to be held within the control limits, including the distance inside the light bulb from the point light source to the incident light path. Taking as an example a wavelength situation wherein a two meter optical path in a normal atmosphere would lead to a 99% absorption. While 99% would normally be unacceptable, if the optical path in an absorbing environment could be reduced to two centimeters, there would then be an about 99% transmission of the light in the optical path and the possibility that sufficient information could be acquired. A theoretical ideal would be where the optical path were sufficiently shortened or where the environment in whatever optical path is used in rendered non or minimally absorbing such as by blowing into the optical path a non absorbing gas to keep the absorption from an information extraction standpoint within a tolerable range. There are structural options such as building the system so that the sample is mostly out of the absorbing optical path that can help but they usually lead to difficult tradeoffs elsewhere in the apparatus and information processing design.

There are many benefits and capabilities that flow from the practice of the invention. Many materials such as $SiO_2$ have a large band gap which means that there is little structure in the optical properties of such materials for characterization using low energy photons, and is why the Reflection Difference Anisotropy technique requires high energies in order for the technique to be useful on large bandgap materials such as silicon carbide (SiC) and gallium nitride (GaN). The invention further has strong benefits for the ellipsometry techniques in which the data analysis uses multiple wavelengths to separate out unknown quantities. In particular in data analysis there is sought combinations of angle of incidence and photon energy range that permit separation and the independent determination of variables of interest. In practice however, the variables are independent functions and thus there is sought photon energies and angles of incidence at which the various component materials have optical properties that vary widely.

Additional benefits from the use of higher energy photons are that they of necessity have short wavelengths (The wavelength $\lambda$ is proportional to 1/ the photon energy E). Since optical determination of film thickness may involve interference fringes, which occur with a spacing of the order of nd/wavelength ($\lambda$), where n is the index of refraction and d is the physical thickness because as the wavelength becomes smaller the fringe spacing will increase where all else remains fixed. A limitation exists in that absorption often increases as energy does so that thinner films may be required to be able to see the fringes. Since light scattering terms scale as the ratio of the particle size to the wavelength, a smaller wavelength will permit observation of smaller particles.

Referring to FIG. 5, a schematic illustration of the principles of the invention is provided. In FIG. 5 the extended photon energy range light source 10 provides light through a range that includes the photon energies wherein the readily distinguishable branches of the signal curves occur as described in connection with FIGS. 2–4.

Examples of preferred light sources currently available in the art that have photon energy ranges up through about 10 eV are deuterium and hydrogen lamps. A reason for the preference is that there is a continuum up through the desired range with these sources. There are other light sources such as arc discharge lamps, hollow cathode lamps and lasers that while the preferred continuum range may not be present still may allow obtaining some desired information.

A controlled ambient 11 throughout the entire light path 12 from the source, through the reflection at 13 and the reflected light path 14 to the detector 15, is provided, the function of which is to prevent such interactions as absorption and local exitation from reducing the distinguishability of the signal delivered to the detector 15. The controlled special ambient 11 may be a normal vacuum (<10 torr) or an inert gas such as helium or nitrogen, that would be nonabsorbing under the conditions involved.

A window member 16 is provided for the light source 10 that performs at least the functions of: not deteriorating or absorbing in passing the desired photon energy range of light; of passing only the desired photon energy range light while preventing any contamination from the light source from entering the ambient; and preventing the ambient from coming into contact with the light source. As examples, some light sources with an above 6 eV photon energy range output may involve an arc and others may involve the element deuterium, both have downside aspects that are undesirable if they get into the ambient. The arc may include unwanted gasses and the deuterium may burn in the atmosphere. The window element 16 should confine any unwanted aspects of the light and any gas generated. It is shown as a single element although it will be apparent that as many individual members as are needed to perform the necessary overall function may be used. While there are many types of windowing component elements available for use in achieving different purposes, the ingredients of any component that is employed must always be able to pass the extended photon range light at the point in the light path where employed without introducing unacceptable attenuation of the light or having the ingredient deteriorate. Windows can be placed at many positions in the optical path, thereby permitting the separation of different ambients and improving component accessibility.

Polarization would be introduced in the incident light path 12 at a location such as 17, and the polarization of the reflected light path 14 would be analyzed at a location such as 18. The polarization component may be passive such as multiple brewster angle reflections, or it may be an active element such as an element with moving parts that can impart rotational polarization. While there are many types of polarization components available for use in achieving different purposes, the ingredients and the optical properties must always be able to achieve the intended purpose without attenuation or deterioration. Where moving parts are involved outgassing of lubricants is a consideration. The material $MgF_2$ has been used in the art for polarizers. In accordance with the invention the materials $MgF_2$ and LiF are suitable for windows and filters. The detector 15 must be responsive to the distinguishing features of the output signal in the reflected light path 14. There a number of types of detectors in the art varying in cost, area covered and sensitivity. The usual detectors in the art employ circuitry selected from photomultiplication, charge coupled device arrays and diode arrays.

The detector element 15 is equipped with a windowing and filtering element 19 that performs the functions of keeping anything from the ambient side out of the detection operation and anything from the detection operation side out of the ambient. While there are many types of windowing and filtering elements that can be used in achieving different purposes, the elements that are employed must always be able to pass the extended photon range of light in the light path without introducing unacceptable attenuation of the light or having the material deteriorate with the passing the incident light. The materials LiF and $MgF_2$ are satisfactory.

In the practice of the invention the photon energy of the light in the light path to the sample property identification or quantification information may affect the selection of component materials. In accordance with the invention, where the desired sample property information is unaffected, a photon energy downshifting element 20 may be employed that performs the function of relaxing some light transmission requirements. In an illustrative example an element of sodium salicyate 20 could be employed to bring the photon range of the signal in the light path 14 as it enters the detector 15 into a range compatible with a more economical photomultiplier than the usual detector with little loss of signal quality.

In the operations in the practice of the invention as depicted in FIG. 5 there will be in the incident light path a beam of photons a well defined angle or range of angles. Referring to FIG. 5 wavelength selection may be performed by using a single wavelength source 10 or by means of a filter, grating or prism, not shown, before any polarizing element 17, in the incident beam 12, or after any polarizing elements 18 in the reflected beam 14.

Once the data has been acquired at the detector 15, the benefits in analysis provided by the combined ability to employ a high photon energy range together with a controlled absorption ambient of the invention become dependent on the type of measurement being performed and the type of information desired.

In the following there will be an example of the particular type of measurement employed in acquiring the information needed for each of the Reflection Anisotropy Spectroscopy system of FIG. 6 and the ellipsometry systems of FIG. 7, which describe detailed descriptions of embodiments of the two general types of characterization technologies.

Referring to FIG. 6 there is illustrated a detailed embodiment of the Reflection Difference Anisotrophy (RDA) application of the principles of the invention as discussed in connection with FIG. 5. In FIG. 6 the special ambient 11 of FIG. 5, is achieved by providing within an enclosure between sides 21 and 22 a controlled ambient 23 of a vacuum or inert gas. The incident light 24, is reflected from the sample 25, at 26, and then into the reflected light 27. The angles $\Phi_1$ and $\Phi_2$ are equal and subtend a combined angle of about 5 degrees. The light source 28 with a window 29 is positioned in the ambient 23 so that the light is reflected from the adjustable arc mirror 30. The adjustability of the arc mirror 30 is provided with a handle 31 that extends through the housing side 21 to permit positioning the incident light 24 on the point 26 on the sample 25 from outside the controlled ambient. A rotational polarizer 32 is provided to set the polarization of the incident light 24. The incident light 24 then passes through an aperture stop 33 positioned a distance "D" about 10 inches from the point 26 on the surface of the sample 25. The reflected light 27 is reflected from an arc mirror 34 with an adjusting handle 35 permitting outside focusing of the reflected light 27 to alignment with an entrance slit 36 into a monochronometer 37 and detector 38 and thence at 39 to an amplifier and computer outside the controlled ambient.23.

Continuing to refer to the Reflection Anisotropy Spectroscopy system as described in connection with FIG. 6, the angle of incidence $\Phi_1$ is close to the normal, depicted as a dotted line between $\Phi_1$ and $\Phi_2$ from the point of reflection 26, which permits specular reflection or the equality of the angle of incidence and the angle of reflection, to be assumed; and scattered light from the sample to be able to be removed from consideration in the analysis. The parameters that are to be determined are the changes in polarization in two orthogonal directions applied at element 32, as sensed at elements 36–39, as relative intensity and phase of the reflected light 27.

The polarization dependent differences in intensity and phase arise from non isotropic optical properties in the sample. Since differences in intensity and phase should be zero for samples for such materials as Silicon (Si), Gallium Nitride (GaN) and cubic Silicon Carbide (SiC), as well as the basal plane of hexagonal materials, then, in analysis strong intensity and phase signals indicate departures from normal atomic symmetry of the sample. Tabulations are assembled of the spectral dependence of these types of signals, compared with theoretical calculations of such spectra inferring signal to type of sample symmetry correlation. An example of this, discussed in connection with FIG. 4, is the relationship between observed spectra and the derivative of bulk dilectric function caused by the presence of a large number of steps at the sample surface. In turn this provides a diagnostic of the type of surface morphology forming during growth of a layer of material. Such a diagnostic is of great value because in growing material, if conditions depart from optimum, morphologies as they become rougher render the grown material less useful than desired.

The second general type of characterization involving an ellipsometry system is illustrated in connection with FIG. 7.

Referring to FIG. 7 there is illustrated a detailed embodiment of an ellipsometric application of the principles of the invention as discussed in connection with FIG. 5. In FIG. 7 the special ambient 11 of FIG. 5, is achieved by providing a housing 50 surrounding a vacuum or inert gas. The housing 50 has a central section 51 in which the sample 52 with the reflection 53 off the surface 54 are located. The housing 50 further has an arm 55 for the incident light and an arm 56 for the reflected light portion of the light path. The light source 57 is positioned on a branch 58 of the arm 55 with a window 59 (permitting branch 58 to have a different controlled ambient, if desired) through which the light enters the arm 55 and is reflected from an adjustable mirror 60 which facilitates focusing of the light path in the housing 50 to the reflection location 53 on the surface 54 of the sample 52. The alignment of the sample 52 is facilitated through the use of a standard autocollimator 61 and glass window 62. Positioning of the sample 52 and alignment of the reflected light portion of the light path is facilitated using a goniometer, not shown, on which the sample may be mounted. The polarization of the incident light in the light path is provided through a fixed polarizer 63 and rotating polarizer 64 assembly and the measurement of the elliptical polarization of the reflected portion of the light path is provided with polarizer 65. In the embodiment of FIG. 7 controlled ambient of the invention 66 is of nitrogen, the light that includes the up through 10 eV photon range of the invention 57 is of deuterium, having a window 59 of $MgF_2$ or LiF. All polarizers are single crystals of $MgF_2$.

The system of FIG. 7 is susceptible to a wide variety of analytical uses. In standard ellipsometry, referring to FIG. 7 specular reflection where the angle of incidence and the angle of reflection are equal are assumed. The characterization is is achieved through the use of two parameters caused by the reflection from the sample. The parameters are: the change in the ratio of reflected intensity in the two orthogonal directions, known in the art as TanPsi ($\Psi$), and the change in the phase difference between two different polarization states, known in the art as Cos Delta ($\Delta$).

In the illustration under discussion, that of the semiconductor industry, in the processing there are situations where it is necessary to determine the thickness and composition of several layers. To make such determinations routinely it is necessary to establish the value of the dilectric constant of the materials under study. A model is then set up of the sample structure in which the layers and interfaces to be involved in the characterization to be performed are assumed, typically approximated by a version of the effective medium approximation either of the bulk end point constituents or intermediate separate measured compositions. From the sensitivity and accuracy that becomes available through the invention, within the background of the model sufficient accuracy is achieved calculations can establish the optical response that the sample of the material under study provides in comparison to experimentally determined results. With computerized iteration and parameter modification, discrepancies are thus reduced between the model and the experimental results. When agreement is sufficiently close, as defined as being within the statistically determined error bounds in the necessary parameters, there will then have been achieved a measurement of the parameters involved. The measured parameters are all well defined and reproducible. The technique being described is the application of the invention to the standard least squares fitting techniques used in the art. In all least squares type fitting care and cross checking is always advisable to make sure that the model remains correct, that the initial parametric assumptions remain valid and that the proper local minimum for the errors is being used.

There are occasions in characterization operations where it is advantageous to simple determine the dielectric spectrum of a material. Where the sample of the material is opaque, sufficiently thick and atomically smooth, the ellipsometric parameters may be inverted to directly provide the dielectric function of the material. With the sensitivity and accuracy achieved in accordance with the invention with the system of FIG. 7, the following equations 1 and 2 are employed. The equations are the types standard in the art and reported by T. E. Faber and N. V. Smith in the Journal of the Optical Society of America, 58, 102,(1968).

$$\epsilon = (SIN^2\Phi TAN^2\Phi(COS^22\Psi - SIN^22\Psi SIN^2\Delta)/(1+COS\Delta SIN\Psi)^2) + SIN^2\Phi \qquad \text{Eq. 1}$$

$$\epsilon = (2SIN^2\Phi TAN^2\Phi(SIN2\Psi - COS2\Psi SIN\Delta)/(1+COS\Delta SIN2\Psi)^2 \text{Eq. 2}$$

Where $\Phi$ is the angle of incidence.

Where the conditions of the equations are not met, various models and approximations may be used to obtain an estimate of the true dielectric function of the material of the sample.

In a scattering form of bidirectional ellipsometry, as could be accomplished using the system of FIG. 7, there cannot be an assumption of specular reflection. In this type of ellipsometry both the angle of incidence but also the scattered angles are important experimental parameters. There are two scattered angles, the one within the incident plane and the one away from the incident plane. This type of ellipsometry is useful in the type of characterization involving the Bidirectional Reflectance Distribution Function (BRDF) reported in the cited Gormer et al reference. The BRDF type characterization is useful with microrough silicon samples. The data is assembled using Equation 3.

$$BRDF = (16\pi^2\lambda^{-1})COS\Phi_1 \, COS\Phi_r \, S_f\Sigma/qjke_ie_k/^2 \qquad \text{Eq. 3}$$

where

Jones matrix formulization is employed $\Phi_1$ is the incident angle $\Phi_r$ is the polar scattering angle S (f) is the surface height function f is the two dimensional spatial frequency in the plane of the surface $e_l$ and $e_k$ are the elements of the unit Jones vectors of the incident and scattered fields, and, q,j, and k are the polarization scattering terms The data assembled is amenable to a powerful simplification in that, when the sum of all four polarization terms at each angle are normalized all explicit dependance on wavelength () and surface height function (S(f)), is removed. It must be remembered and taken into consideration where needed that such a simplification suppresses amplitude variation away from specular. Varying ($\lambda$) will vary the index of refraction, thereby varying the q,j,k terms.

In the case of silicon on insulator structures with a 200 nm silicon layer varying ($\lambda$) will impact the appropriateness of the model used. For ($\lambda$)<350 nm only the surface region will be proded whereas for ($\lambda$)>500 nm the full structure must be accounted for. Thus, measurement with ($\lambda$)<350 nm may be interpreted with this microroughness model.

What has been described is a technique of reflected light characterization of solid materials that employs extending the photon energy range of the light that is used in connection with a controlled ambient and this in turn unmasks more detailed features of differences in the material under study for analysis.

What is claimed is:

1. In apparatus for the characterization of a solid of the type where changes in the polarization of light in a light path in which said light has passed in an incident light beam from a light source to said solid and after reflection from a point on the surface of said solid in a reflected beam to a detector of said changes, said changes being correlated with features of said solid, the improvement comprising:

a deuterium light source providing light through an MgF window into a light path in a controlled ambient of one of a vacuum and an inert gas in an enclosure including light path aiming from outside said enclosure, said light in said light path including a photon energy range up through and including 10 eV, said light in said path being polarized before reflection from said solid, said light path extending from said light source to a detector of changes in polarization of said light after reflection from said solid, and, said incident light beam and said reflected light beam subtend an angle that is within about 5 degrees of the normal from the surface of said solid.

2. In apparatus for the characterization of a solid of the type where changes in the polarization of light in a light path in which said light has passed in an incident light beam from a light source to said solid and after reflection from a point on the surface of said solid in a reflected beam to a detector of said changes, said changes being correlated with features of said solid, the improvement comprising:

a deuterium light source providing light through an MgF window into a light path in a controlled ambient of one of a vacuum and an inert gas in an enclosure, including light path aiming from outside said enclosure, said light in said light path including a photon energy range up through and including 10 eV, said light in said path being polarized before reflection from said solid, said light path extending from said light source to a detector of changes in polarization of said light after reflection from said solid, and, said incident light beam and said reflected light beam subtend equal angles with respect to said surface of said solid, said controlled ambient being housed in a central region surrounding the point of reflection from said solid with separate controlled ambient containing arms for each of said incident and said reflected light beams, and, said light aiming including a capability for focusing said incident light beam on said point on the surface of said solid that is adjustable from outsise the housing of said ambient.

3. A high sensitivity and signal distinguishing ability metrology apparatus comprising:

a light path including; a deuterium light source with an MgF window component, an incident light beam, an initial polarizer component, reflection from the surface of a sample of a solid under study, a reflected light beam and a sensing capability for changes in said reflected light beam that are imparted into said reflected light beam in said reflection from said surface, wherein, said light path being in a signal absorption controlled ambient, said incident light beam and said reflected light beam are each at a small angle with respect to the normal of said surface of said sample, said sensing capability identifies changes in reflectivity in said light beam, said controlled ambient is one of an inert gas and a normal vacuum, and, said controlled ambient is in a housing with capability for adjustment of the reflection point on said surface of said sample of said incident light beam extending outside said housing.

4. A high sensitivity and signal distinguishing ability metrology apparatus comprising:

a light path including; a deuterium light source component, an incident light beam, an initial polarizer component, reflection from the surface of a sample of a solid under study, a reflected light beam and a sensing capability for changes in said reflected light beam that are imparted into said reflected light beam in said reflection from said surface, wherein, said light source component having a photon range up through and including about 10 eV and light path being in a signal absorption and signal definiteness limitimg controlled ambient, said incident light beam and said reflected light beam are each at a small angle with respect to said surface of said sample and said sensing capability includes polarization analysis and identifies changes in polarization in said reflected light beam light, said light source component is a deuterium light source with an MgF window member separating the light point in said component from said controlled ambient, said controlled ambient is one of an inert gas and a normal vacuum and, said light path is in said controlled ambient in a housing with a central sample reflection region with separate arms for said incident and said reflected light beams housing with capability for adjustment of the reflection point on said surface of said sample of said incident light beam extending outside said incident light beam arm of said housing and with autocollimator capability for adjustment of the position of said sample in said central sample reflection region of said housing.

5. The method of improving the sensitivity and signal distinguishing ability of reflected light characterization of solids, comprising in combination the steps of:

providing a light path including a serial assembly of; a light source component, an incident light beam, an initial polarizer component, reflection from the surface of a sample of a solid under study, a reflected light beam and a sensing capability for changes in said reflected light beam that are imparted into said reflected light beam in said reflection from said surface, providing in said light source component a photon energy range up through about 10 eV, and, enclosing all of said light path in a signal absorption and signal definiteness limiting controlled ambient, and wherein, in said providing said light source component step there is provided a continuum photon energy range up through about 10 eV, the additional step of providing in said light path an incident light beam direction and a reflected light beam direction combination whereby said incident light beam and said reflected light beam are each at a small angle with respect to the normal of said surface of said sample and said sensing capability identifies changes in reflectivity in said light beam, further including the steps of providing in said light source component, a deuterium light source with an MgF window member separating the light point in said component from said ambient, enclosing said light path in a controlled ambient said controlled ambient being one of an inert gas and a normal vacuum and, maintaining said controlled ambient in a housing with capability for adjustment of the reflection point on said surface of said sample of said incident light beam extending outside said housing.

6. The method of improving the sensitivity and signal distinguishing ability of reflected light characterization of solids comprising in combination the steps of:

providing a light path including a serial assembly of; a light source component, an incident light beam, an initial polarizer component, reflection from the surface of a sample of a solid under study, a reflected light beam and a sensing capability for changes in said reflected light beam that are imparted into said reflected light beam in said reflection from said surface, providing in said light source component a continuum photon energy range up through about 10 eV, and, enclosing all of said light path in a signal absorption and signal definiteness limiting controlled ambient, and further, including the steps of;

arranging that said incident light beam and said reflected light beam are each at a small angle with respect to said surface of said sample and said sensing capability includes polarization analysis and identifies changes in polarization in said reflected light beam light beam, providing as said light source component a deuterium light source with an MgF window member separating the light point in said component from said controlled ambient, enclosing said light path in a controlled ambient said controlled ambient being one of an inert gas and a normal vacuum, and, maintaining said controlled ambient in a housing with capability for adjustment, of the reflection point on said surface of said sample, of said incident light beam, extending outside said housing.

* * * * *